United States Patent [19]

Matsubara et al.

[11] 4,238,479

[45] Dec. 9, 1980

[54] NUTRIENT TREATING NUTRITIONAL DEFICIENCY

[75] Inventors: Masaka Matsubara, Tokyo; Tatsuo Ishihara, Tokyo, both of Japan; Tokitaka Mori, 1-24, Sakuradai, Nerima-ku, Tokyo, Japan

[73] Assignee: Tokitaka Mori, Tokyo, Japan

[21] Appl. No.: 10,050

[22] Filed: Feb. 7, 1979

[30] Foreign Application Priority Data

Feb. 24, 1978 [JP] Japan .................................. 53-20720

[51] Int. Cl.³ ..................... A61K 35/12; A61K 35/56; A61K 35/78
[52] U.S. Cl. ........................................ 424/95; 424/195
[58] Field of Search ................................. 424/195, 95

[56] References Cited

U.S. PATENT DOCUMENTS

| | | | |
|---|---|---|---|
| 2,959,580 | 11/1960 | Shlenk et al. | 536/103 |
| 3,061,444 | 10/1962 | Rogers et al. | 536/103 |
| 4,054,736 | 10/1977 | Hayashi et al. | 536/103 |

OTHER PUBLICATIONS

Matsuba–Chem. Abst., vol. 73 (1970), 28906f.
Matsubara et al.–Chem. Abst., vol. 88 (1978) 65, 958e.
Matsubara et al.–J. Med. Soc. Toho Univ., vol. 24, No. 2, Feb. 1977, pp. 252–261.

Primary Examiner—Stanley J. Friedman
Attorney, Agent, or Firm—Frishauf, Holtz, Goodman & Woodward

[57] ABSTRACT

A method of treating humans suffering from a nutritional deficiency by administering an orally ingestible nutrient composition comprising a substance obtained by extraction of Paramecium thereby providing nutrition to the body with a resultant invigorating effect on the human body. The preferred compositions contain both the lower molecular weight portion and the higher molecular weight portions which are obtained from the extract of Paramecium. It is particularly preferred to utilize the nutrient composition wherein said extract is combined with a clathrate compound, particularly cyclodextrin.

12 Claims, No Drawings

NUTRIENT TREATING NUTRITIONAL DEFICIENCY

FIELD

This invention relates to a nutrient having an invigorating effect on human body. More particularly, this invention relates to a nutrient comprising substance obtained by extraction of Paramecium.

PRIOR ART

Paramecium is well known as one of unicellular protozoa. Journal of Medical Society of Toho, Vol. 24, No. 2 pages 252–261 (1977) reports that a water-soluble component of Paramecium brings about cancer-inhibiting effect or other desease-inhibiting effects on human body when administered hypodermically.

SUMMARY OF THE INVENTION

We have now found that substance obtained by extraction of Paramecium with water or aqueous solution can bring about an invigorating effect on human body when taken into orally. We have further found that a combination of a lower molecular (weight) portion and a higher molecular (weight) portion, both portions being separated from an extract obtained by extraction of Paramecium with water or aqueous solution, can bring about the invigorating effect more prominently. We have further found that the active components of the substance obtained by the extraction can show the invigorating effect more prominently when taken into human body in the form of a clathrate compound with a certain host compound.

In accordance with the findings stated above, the present invention provides a nutrient having a prominent invigorating effect.

DETAILED DESCRIPTION OF INVENTION

Paramecium that can be employed in this invention may be exemplified by the following, but is not limited thereto:

Paramecium (P.) aurelia, P. bursaria, P. calkinsi, P. caudatum, P. multimieulonueleatum, P. polycaryum, P. trichium, P. woodruffi, Killer Paramecium.

The extraction can be carried out by the use of water or aqueous solution. The water or aqueous solution preferably has pH value of about 5.5 when the extraction is done. The aqueous solution may contain a small amount of one or more of a pH regulating agent and inorganic and organic salts. The aqueous solution may be a buffer solution. The aqueous solution may contain an organic solvent such as alcohol, ether or ketone that is miscible with water.

The extraction of Paramecium can be carried out in any of conventional ways. The aqueous extract resulting from the extraction procedure can be concentrated under reduced pressure or by evaporation, or dried to solid by freeze-drying or under reduced pressure. The concentrated or dried extract thus obtained can be incorporated in a nutrient of this invention with no further treatment. However, it is preferred to employ substance that is obtained by further treatment of these extracts so as to get more prominent effect.

The further treatment described above may be done by recovering two principal portions from the extract by a separation method. Examples of the separation method include dialysis, ultrafiltration, gel-filtration and a method utilizing an organic solvent. However, other suitable methods can be likewise employed. In the context of this specification, the term "further treatment" means procedure for separating a higher molecular portion and a lower molecular portion both of which are contained as active components in the extract.

Examples of illustrative procedures of the further treatment are described below more in detail.

FREEZE-DRYING PROCEDURE

This procedure is applied when the need arises.

An aqueous Paramecium suspension which has been kept frozen is thawed, made somewhat acidic (around pH 5.5), and heated with stirring for one hour in a water bath maintained at 70° C. The suspension is then cooled and centrifuged to separate the supernatant (extract) from the precipitate. To the separated precipitate is added an appropriate amount of water to make the suspension acidic as above, and the resulting suspension is likewise heated with stirring for one hour in a water bath maintained at 80° C. The supernatant is separated after centrifugation, and the precipitate thus obtained is again heated as above except for replacing the bath temperature from 80° C. to 90° C. Three portions of the supernatants (extracts) are combined and concentrated under reduced pressure. If desired, the supernatants may be dried under reduced pressure.

The concentrated supernatant can be treated, for example, in the following manner to recover two fractions containing the active components. The dried product can be employed for the following procedure in the form of an aqueous solution after being dissolved in water.

FRACTIONATION PROCEDURES

(a) Dialysis

The dialysis is carried out by means of the dialysis film such as cellulose film (e.g. Visking ® Tubing available from Visking Company, U.S.A.) to separate a fraction going out through the film from the remaining fraction. The following example shows the procedure more in detail.

In 50 ml. of water was dissolved 0.9 g. of the freeze-dried extract, and the solution is placed in Visking Tubing (for fractionating by M. W. approx. 5,000). The dialysis was made at 5° C. for 48 hours in water of 500 ml. The dialysis was further continued for 24 hours after replacing 500 ml. of fresh water for the used water. The outer aqueous phases were combined and concentrated under reduced pressure to leave a residue of about 50 ml., which was then freeze-dried. The inner aqueous phase was treated in the same manner.

Yields:
Fraction (I)—obtained from the inner phase—consisting mainly of higher molecular portion; 21 mg.
Fraction (II)—obtained from the outer phases—consisting mainly of lower molecular portion; 195 mg.

(b) Ultrafiltration

The aqueous solution adjusted for fractionation is applied to ultrafiltration film for separating a fraction (I) not going through the film from a fraction (II) going through the film. Examples of the ultrafiltration film include Diafilter ® (available from Bio Engineering Co., Ltd., Japan) and Diaflofilter ® (available from Amicon Corporation, U.S.A.). These films include a variety of products that can be utilized for fractionation by a variety of molecular weight as desired. The following example shows the procedure more in detail.

In 50 ml. of water was dissolved 1.3 g. of the freeze-dried extract, and the solution was placed on an ultrafiltration apparatus provided with Diaflo UM-10 (for fractionation by M.W. 10,000) and received the nitrogen pressure of 4 Kg/cm$^2$ by means of a nitrogen bomb. When the solution on the filter decreased to 10 ml., 50 ml. of water was added to the solution, and the filtration was further continued. Then the concentrated solution on the filter was taken out when the volume reached 15 ml. The concentrated solution taken out and an aqueous phase having gone through the filter were separately freeze-dried.

Yields:
Fraction (I)—obtained from the concentrated solution—consisting mainly of higher molecular portion; 300 mg.
Fraction (II)—obtained from the aqueous phase having gone through—consisting mainly of lower molecular portion; 540 mg.

(c) Gel-filtration

The aqueous solution adjusted for fractionation is placed on a column of gel-filtration material such as Sephadex ® (available from Phamacia-Fine Chemicals A. B., Uppsala, Sweden) or Biogel ® (available from Biorad Laboratories, U.S.A.). Then, Fraction (I) is collected initially and Fraction (II) is collected afterwards. The following example shows the procedure more in detail.

In 10 ml. of water was dissolved 1.5 g. of the freeze-dried extract. The supernatant (10 ml.) of the solution was placed on a column (diameter; 2.5 cm: length; 38 cm.) of Sephadex G-25, and eluted with water. Every 5 ml. of the fraction was collected by means of Fraction Collector. The detections of the dissolved components were carried out by observing UV absorption spectra at 260 m$\mu$ and 490 m$\mu$ (the latter being based upon Phenol-Sulfuric Acid Method). According to the elution curve, fractions were combined into four groups, and Fraction (I) consisting of the first group and Fraction (II) consisting of three groups collected afterwards were separately freeze-dried.

Yields:
Fraction (I)—consisting mainly of higher molecular portion; 142 mg. (fraction Nos. 16–25)
Fraction (II)—consisting mainly of lower molecular portion; 500 mg. (fraction Nos. 26–42), 9 mg. (fraction Nos. 46–55) and 10 mg. (fraction Nos. 56–65)

(d) Fractionation with aqueous organic solvent

To the aqueous solution adjusted for fractionation is added an organic solvent freely miscible with water, the amount of the latter being several times as much as the former. The supernatant thus obtained (Fraction (II)) is separated from the deposited precipitate (Fraction (I)) and, after concentration under reduced pressure, freeze-dried. The following example shows the procedure more in detail.

In 140 ml. of water was dissolved 7 g. of the powdery freeze-dried extract, and 700 ml. of ethyl alcohol was added thereto. After being left overnight in a chilled room, the mixture was centrifuged for 15 minutes at 10,000 rpm. The precipitate was separated from the supernatant. To the precipitate was added 250 ml. of ethyl alcohol, and the mixture was, after being left overnight in a chilled room, centrifuged for 15 minutes at 10,000 rpm. The two supernatant portions separated from the precipitate (Fraction (I)) were combined, concentrated under reduced pressure and freeze-dried to give Fraction (II).

Yields:
Fraction (I)—consisting mainly of higher molecular portion; 0.55 g.
Fraction (II)—consisting mainly of lower molecular portion; 4.97 g.

The dried extract (A) treated with no separation procedure and two fractions (B) and (C) separated therefrom have the following characteristics. Fractions (B) and (C) mentioned in the following column are obtained by the gel-filtration employing Sephadex G-25 and correspond to the previously cited Fractions (I) and (II), respectively.

Solubility:
(A)—partially soluble in water and ethyl alcohol, almost insoluble in ethyl ether
(B)—soluble in water, insoluble in ethyl alcohol, almost insoluble in ethyl ether
(C)—readily soluble in water and ethyl alcohol, almost insoluble in ethyl ether UV absorption spectrum: All (A, B and C) have an absorption peak in the area of 240–280 m$\mu$ Absorption intensity:
(B)—$E_{1\ cm.}^{1\%}$ 45.6
(C)—do. 9.5

Molecular weight:
(A)—mixture of higher molecular portion and lower molecular portion
(B)—more than approximately 5,500
(C)—less than approximately 5,500

| Characteristic reactions: | (A) | (B) | (C) |
| --- | --- | --- | --- |
| Phenol - Sulfuric acid Method | (+) | (+) | (+) |
| Somogyi - Nelson Method | (+) | (+) | (+) |
| Diphenylamine Method | (+) | (−) | (+) |
| Ninhydrin Reaction | (+) | (+) | (+) |
| Buret Reaction | (+) | (+) | (+) |
| Folin Method (variation of Lowry Method) | (+) | (+) | (+) |

In view of the above description, principal (active) components of these extracts and fractions are considered to be glycoproteins containing nucleic acid.

Toxicity test: Each of (A), (B) and (C) was daily administered orally into mouse in the amount of 50 mg./kg. for six weeks. No change has been observed. Alternatively, the amount of 500 mg./kg. for 4 weeks has been tried and no change has been observed.

The extract (A) and Fractions (I) and (II) can be admixed with an appropriate carried to produce a nutrient of this invention. There is no specific limitation on the carrier, so far as it does not cause harmful effects on human body when taken orally. Examples of the appropriate carrier include royal jelly and lactose. Any food for human beings can be also mentioned as the appropriate carrier. The nutrient of this invention can be orally taken into human body in the form of pellet, tablet, granula, powder, paste, liquid, aqueous solution or suspension, etc.

The extract (A), Fractions (I) and (II) and mixtures thereof are given in a small amount per day to human body. Generally, the amount does not exceed 50 mg. per day, and ordinally an amount of not more than 10 mg. may be given a day. Accordingly, the nutrient of this invention generally comprises the extract (A), Fractions (I) and/or (II), and/or their mixtures in an amount of not more than 50 mg., and more specifically of not more than 10 mg. For general purpose of invigorating human body, mixtures of Fractions (I) and (II) are preferably employed. A mixture of Fractions (I) and (II) may preferably be in a ratio of approximately 1:1 = 1:10,000 ((I):(II)).

As described hereinbefore, the extract (A) and Fractions (I) and (II) can invigorate human body when taken into orally. A carrier can be employed for convenience's sake. Moreover, these extract and fractions show more prominent invigorating effect when they are taken into in the form of clathrate compound of their active components with an appropriate host compound. When the active component is taken into human body in the form of a clathrate compound, in other word, when the active component is taken into under protection of other compounds, the active component can pass through the stomach with no serious decomposition or deterioration and reach the intestine where the active component can be absorbed. Consequently, the active component taken into body in that manner can work more efficiently.

There is no specific limitation on the host compound used in this invention, as far as it is not harmful for human body and is capable of forming a clathrate compound with the active component of substance obtained by extraction of Parmecium with water or aqueous solution. Throughout the present specification and claims, the phrase "substance obtained by extraction of Paramecium with water or aqueous solution" or term "the extracted substance" includes the aforementioned extract (A) and Fractions (I) and (II). The appropriate host compound can be exemplified by cyclodextrin in any of alfa, beta and gamma forms. Preferred is beta-cyclodextrin.

The host compound is admixed with the extract (A) and/or Fractions (I) and/or (II) generally in a ratio of more than 1:5 by weight (host compound: extract (A), etc.). There is no upper limit of the admixed host compound, because the host compound can be utilized as a carrier.

There is no specific limitation on a method for admixing the extracted substance and a carrier. There also is no specific limitation on the method for admixing the extracted substance, a host compound and a carrier. However, if a host compound is to be admixed into a neutrient, the extracted substance and the host compound are preferably admixed prior to addition of a carrier so as to form a clathrate compound more efficiently.

Examples of a method for forming a clathrate compound include (i) a method comprising admixing and kneading the extracted substance, a host compound and water, and (ii) a method comprising addition of the extracted substance to an aqueous solution of a host compound.

The following examples are provided to show more in detail but not to limit the present invention.

EXAMPLE 1

Ten mg. of the extract (A) and 90 mg. of loyal jelly were admixed to form a neutrient.

EXAMPLE 2

Five mg. of Fraction (I), 10 g. of Fraction (II) and 1 kg. of lactose were admixed enough to form a uniform powdery neutrient.

EXAMPLE 3

Five mg. of Fraction (I) and 10 g. of Fraction (II) were sufficiently admixed and then dissolved in 10 ml. of distilled water. To the resulting solution was added 30 g. of beta-cyclodextrin. The mixture was then stirred to become pasty, and the pasty mixture was kneaded in a mortar for about 5 hours.

Forty grams of the above-obtained paste and 4,950 g. of lactose were admixed in a mortar to form a uniform mixture.

EXAMPLE 4

In 165 ml. of an aqueous solution saturated with beta-cyclodextrance (prepared by dissolving 1.85 g. of beta-cyclodextrane in 100 ml. of distilled water) were dissolved 1 mg. of Fraction (I) and 3 g. of Fraction (II), by stirring for about 5 hours. The solution thus obtained was then freeze-dried and kept.

Four grams of the freeze-dried product and 496 g. of lactose were admixed in a mortar to form a uniform mixture.

EXAMPLE 5

Female of age 49 who had been sufferring from stiffness of the shoulders, headache, lack of appetite and other bad physical conditions and had been receiving acupuncture treatment once a month was being orally given one gram of a nutrient prepared in Example 3 (or Example 4) twice a day. This procedure was since then continued. After 30 days from the beginning of taking the nutrient, the lack of appetite diminished, and the stiffness of shoulders and headache gradually reduced. Other bad physical conditions became hardly shown. Accordingly, the acupuncture treatment of once a month became unnecessary.

EXAMPLE 6

Male of age 67 who had suffered from tuberculosis of the lungs at age 20 and since then received medical treatment for 10 years was of weak constitution even after end of the treatment. For instance, he was apt to catch a cold when he was exposed to cold atmosphere after bathing. Then, he sometimes suffered from bronchitis which needed medical treatment in a hospital. He was given the nutrient of the present invention in the manner described in Example 5. After two weeks from the beginning of taking the nutrient, he became to be apt hardly to catch a cold even after bathing, and his physical conditions and activities became improved.

EXAMPLE 7

Female of age 76 who had been suffering from lack of apetite and under depression of spirits and physical conditions was given the nutrient of the present invention in the manner described in EXAMPLE 5. After one week from the beginning of taking the nutrient, her appetite became improved and she was observed to be getting physical conditions improved.

EXAMPLES 8–22

In the same way as in Examples 5-7, 15 people (male and female) were treated and there were observed prominent improvement of physical conditions for 10 people and noticeable improvement of physical conditions for 5 people.

What is claimed is:

1. A method of treating nutritional deficiency in a human comprising orally administering to a human in need of treatment therefor a nutritionally effective amount of an orally ingestible nutrient composition, said nutrient composition comprising a small amount of substance obtained by extraction of Paramecium with water or aqueous solution and a large amount of a carrier, said nutritionally effective amount of said nutrient composition being an amount such that the total of said substance extracted from Paramecium ingested per day does not exceed 50 mg.

2. The process of claim 1, wherein said substance is dried extract of Paramecium.

3. The process of claim 1 or claim 2, wherein said substance consists essentially of a major amount of a lower molecular weight portion and a minor amount of a higher molecular weight portion, both portions being separated from extract of Paramecium.

4. The process of claim 1, wherein said nutrient composition also contains cyclodextrin.

5. The process of claim 3, wherein said nutrient composition also contains cyclodextrin in the beta form.

6. The process of claim 1, wherein said carrier is lactose.

7. The process of claim 5, wherein said carrier is lactose.

8. The process of claim 1, wherein said carrier is royal jelly.

9. The process of claim 5, wherein said carrier is royal jelly.

10. The process of claim 1, wherein said substance essentially consists of a lower molecular weight portion which is separated from the extract of Paramecium.

11. The process of claim 1, wherein the total of said substance extracted from Paramecium ingested per day does not exceed 10 mg.

12. The process of claim 5, wherein the total of said substance extracted from Paramecium ingested per day does not exceed 10 mg.

* * * * *